United States Patent [19]

Kawai et al.

[11] 4,444,591

[45] Apr. 24, 1984

[54] CHROMOGENIC COMPOUNDS AND THE USE THEREOF AS COLOR FORMER IN COPYING OR RECORDING MATERIALS

[75] Inventors: Hajime Kawai, Jyoyo; Katsuhiko Tsunemitsu, Kyoto; Yoshiharu Fujino; Yoji Shimizu, both of Kyoto, all of Japan

[73] Assignee: Yamada Chemical Co., Ltd., Kyoto, Japan

[21] Appl. No.: 351,600

[22] Filed: Feb. 23, 1982

Related U.S. Application Data

[63] Continuation-in-part of Ser. No. 929,724, Jul. 31, 1978, abandoned.

[30] Foreign Application Priority Data

Aug. 8, 1977 [JP] Japan .................................. 52-92270

[51] Int. Cl.³ .................. C07D 497/10; C09D 3/00
[52] U.S. Cl. .................................. 106/21; 106/137; 106/193 D; 106/214; 523/161; 524/22; 524/44; 524/45; 524/46; 524/47; 524/110; 524/114; 549/265
[58] Field of Search .................. 106/21; 523/161; 524/110, 114; 549/526, 265

[56] References Cited

U.S. PATENT DOCUMENTS

3,996,405 12/1976 Porter .................................. 428/307

FOREIGN PATENT DOCUMENTS

| 2262127 | 12/1972 | Fed. Rep. of Germany . |
| 47-34422 | 11/1972 | Japan . |
| 48-62506 | 8/1973 | Japan . |
| 49-28410 | 3/1974 | Japan . |
| 49-33714 | 3/1974 | Japan . |
| 49-32767 | 8/1974 | Japan . |
| 1277545 | 6/1972 | United Kingdom . |
| 1306263 | 2/1973 | United Kingdom . |
| 1459417 | 12/1976 | United Kingdom . |

*Primary Examiner*—Allan Lieberman
*Attorney, Agent, or Firm*—Wegner & Bretschneider

[57] ABSTRACT

Novel chromogenic fluoran compounds of the formula:

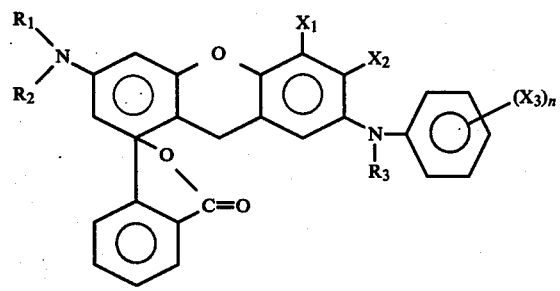

wherein $R_1$ is selected from the group consisting of alkyl radicals of from five to eight carbon atoms; $R_2$ is selected from the group consisting of alkyl radicals of from one to eight carbon atoms; $R_3$ is selected from the group consisting of hydrogen atom and lower alkyl radicals of from one to four carbon atoms; $X_1$ and $X_2$ are independently selected from the group consisting of hydrogen atom and lower alkyl radicals of from one to four carbon atoms, $X_3$ is selected from the group consisting of hydrogen atom, lower alkyl radicals of from one to four carbon atoms, halogen atoms and trifluoromethyl radical; and n is an integer of a value of 1 or 2; providing that $R_1$ does not represent an amyl radical when $R_2$ is selected from the group consisting of alkyl radicals of from one to five carbon atoms, $X_1$ and $X_2$ are each a hydrogen atom, $X_3$ is selected from the group consisting of hydrogen atom, lower alkyl radicals of from one to four carbon atoms and halogen atoms.

2 Claims, No Drawings

CHROMOGENIC COMPOUNDS AND THE USE THEREOF AS COLOR FORMER IN COPYING OR RECORDING MATERIALS

CROSS-REFERENCE TO RELATED APPLICATION

This application is a continuation-in-part of our co-pending application Ser. No. 929,724 filed July 31, 1978 and now abandoned.

SUMMARY OF THE INVENTION

In a first aspect of the invention there is provided a chromogenic compound of the general formula:

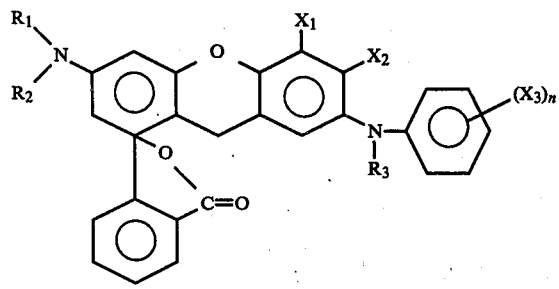

wherein $R_1$ is selected from the group consisting of alkyl radicals of from five to eight carbon atoms; $R_2$ is selected from the group consisting of alkyl radicals of from one to eight carbon atoms; $R_3$ is selected from the group consisting of hydrogen atom and lower alkyl radicals of from one to four carbon atoms; $X_1$ and $X_2$ are independently selected from the group consisting of hydrogen atom and lower alkyl radicals of from one to four carbon atoms, $X_3$ is selected from the group consisting of hydrogen atom, lower alkyl radicals of from one to four carbon atoms, halogen atoms and trifluoromethyl radical; and n is an integer of a value of 1 or 2; providing that $R_1$ does not represent an amyl radical when $R_2$ is selected from the group consisting of alkyl radicals of from one to five carbon atoms, $X_1$ and $X_2$ are each a hydrogen atom, $X_3$ is selected from the group consisting of hydrogen atom, lower alkyl radicals of from one to four carbon atoms and halogen atoms.

In a second aspect of the invention, there is provided a color developing composition suitable for use in pressure- or heat-sensitive copying sheets, comprising at least one chromogenic compound of a chromogenic compound of the general formula:

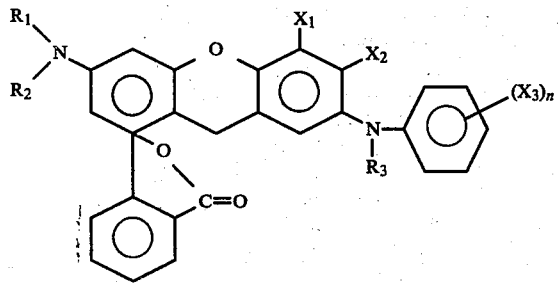

wherein $R_1$ is selected from the group consisting of alkyl radicals of from five to eight carbon atoms; $R_2$ is selected from the group consisting of alkyl radicals of from one to eight carbon atoms; $R_3$ is selected from the group consisting of hydrogen atom and lower alkyl radicals of from one to four carbon atoms; $X_1$ and $X_2$ are independently selected from the group consisting of hydrogen atom and lower alkyl radicals of from one to four carbon atoms, $X_3$ is selected from the group consisting of hydrogen atom, lower alkyl radicals of from one to four carbon atoms, halogen atoms and trifluoromethyl radical; and n is an integer of a value of 1 or 2; providing that $R_1$ does not represent an amyl radical when $R_2$ is selected from the group consisting of alkyl radicals of from one to five carbon atoms, $X_1$ and $X_2$ are each a hydrogen atom, $X_3$ is selected from the group consisting of hydrogen atom, lower alkyl radicals of from one to four carbon atoms and halogen atoms, as a color former dissolved in an organic solvent and contained in microcapsules capable of rupture under pressure or heat and an electron-accepting substance.

DETAILED DESCRIPTION OF THE INVENTION

This invention relates to novel chromogenic fluoran compounds and to the use thereof as color formers in pressure-sensitive and heat-sensitive copying (or recording) sheets.

The novel chromogenic compounds according to the present invention are defined by the following general formula:

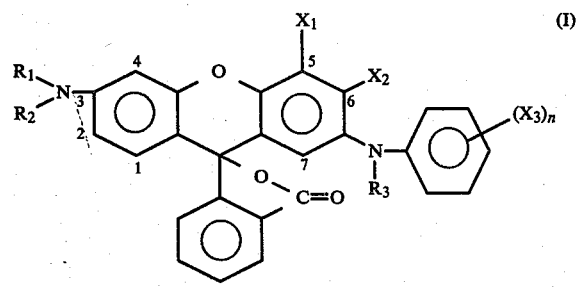

(I)

wherein $R_1$ is selected from the group consisting of alkyl radicals of from five to eight carbon atoms; $R_2$ is selected from the group consisting of alkyl radicals of from one to eight carbon atoms; $R_3$ is selected from the group consisting of hydrogen atom and lower alkyl radicals of from one to four carbon atoms; $X_1$ and $X_2$ are independently selected from the group consisting of hydrogen atom and lower alkyl radicals of from one to four carbon atoms, $X_3$ is selected from the group consisting of hydrogen atom, lower alkyl radicals of from one to four carbon atoms, halogen atoms and trifluoromethyl radical; and n is an integer of a value of 1 or 2; providing that $R_1$ does not represent an amyl radical when $R_2$ is selected from the group consisting of alkyl radicals of from one to five carbon atoms, $X_1$ and $X_2$ are each a hydrogen atom, $X_3$ is selected from the group consisting of hydrogen atom, lower alkyl radicals of from one to four carbon atoms and halogen atoms.

The fluoran compounds of the general formula (I) in themselves are substantially colorless. They, however, have a property such that when they are brought into intimate contact with electron-accepting substances such as, for example organic acids, acid clay, activated clay, phenol formalin resin, metal salts of aromatic carboxylic acids and bisphenol A, the lactone rings in these compounds are opened and give rise to colors of the black group or green group. These compounds, therefore, are suitable particularly as color formers for pressure-sensitive and heat-sensitive copying sheets which are adaptable for the electrophotographic production of copies.

It has now been ascertained that the chromogenic compounds of the present invention notably excel these known counterparts in all or some of the points a through d indicated below.

a. Spontaneous color-forming property in dilute aqueous acid solutions.
b. Solubility in organic solvents.
c. Spontaneous color-forming property exhibited upon application to heat-sensitive sheets.
d. Thermal sensitivity exhibited upon application to heat-sensitive sheets.

These characteristic features, a through d, are highly significant factors, as well recognized in the art, for chromogenic compounds to serve as fully practicable color formers in pressure-sensitive and heat-sensitive copying sheets.

In the chromogenic compounds of the present invention represented by Formula (I), the more useful are those of a class which satisfy the condition that $R_1$ is selected from the group consisting of alkyl radicals of from five to eight carbon atoms, $R_2$ is selected from the group consisting of alkyl radicals of from one to eight carbon atoms, $R_3$ is hydrogen atom or methyl radical, $X_1$ is a hydrogen atom, $X_2$ is hydrogen atom or methyl radical and $X_3$ is selected from the group consisting of hydrogen atom, methyl radical and halogen atom.

It has been ascertained that the compounds of these classes are invariably capable of forming clear black colors and are notably excellent in all the points, a through d, mentioned above. Typical compounds of these classes are 3-(N-methyl-N-n-amyl)-amino-6-methyl-7-anilinofluoran, 3-(N-ethyl-N-n-amyl)-amino-6-methyl-7-anilinofluoran, 3-(N-ethyl-N-iso-amyl)-amino-6-methyl-7-anilinofluoran, 3-(N-di-iso-amyl)-amino-6-methyl-7-anilinofluoran, 3-(N-methyl-N-n-hexyl)-amino-6-methyl-7-anilinofluoran, 3-(N-methyl-N-n-hexyl)-amino-7-anilinofluoran, 3-(N-ethyl-N-n-hexyl)-amino-6-methyl-7-anilinofluoran, 3-(N-ethyl-N-n-hexyl)-amino-7-anilinofluoran, 3-(N-ethyl-N-n-hexyl)-amino-7-(N-methyl-N-phenyl)-aminofluoran, 3-(N-ethyl-N-n-hexyl)-amino-6-methyl-7-(N-p-tolyl)-aminofluoran, 3-(N-ethyl-N-β-ethylhexyl)-amino-6-methyl-7-anilinofluoran, 3-(N-methyl-N-n-amyl)-amino-6-methyl-7-(N-p-tolyl)-aminofluoran, 3-(N-di-n-amyl)-amino-6-methyl-7-anilinofluoran, 3-(N-n-propyl-N-n-hexyl)-7-(N-o-chlorophenyl)-aminofluoran, 3-(N-n-propyl-N-n-hexyl)-6-methyl-7-anilinofluoran, 3-(N-di-n-hexyl)-amino-6-methyl-7-anilinofluoran, 3-(N-ethyl-N-n-heptyl)-7-anilinofluoran, 3-(N-ethyl-N-n-heptyl)-6-methyl-7-anilinofluoran and 3-(N-di-n-octyl)-amino-6-methyl-7-anilinofluoran.

More preferable compounds are 3-(N-methyl-N-n-amyl)-amino-6-methyl-7-anilinofluoran, 3-(N-ethyl-N-n-amyl)-amino-6-methyl-7-anilinofluoran, 3-(N-ethyl-N-iso-amyl)-amino-6-methyl-7-anilinofluoran, 3-(N-di-iso-amyl)-amino-6-methyl-7-anilinofluoran, 3-(N-methyl-N-n-hexyl)-amino-6-methyl-7-anilinofluoran, 3-(N-methyl-N-n-hexyl)-amino-7-anilinofluoran, 3-(N-ethyl-N-n-hexyl)-amino-6-methyl-7-anilinofluoran, 3-(N-ethyl-N-n-hexyl)-amino-7-anilinofluoran, 3-(N-di-n-amyl)-amino-6-methyl-7-anilinofluoran and 3-(N-n-propyl-N-n-hexyl)-7-(N-o-chlorophenyl)-aminofluoran.

Most preferable compounds are 3-(N-ethyl-N-iso-amyl)-amino-6-methyl-7-anilinofluoran, 3-(N-methyl-N-n-hexyl)-amino-6-methyl-7-anilinofluoran and 3-(N-ethyl-N-n-hexyl)-amino-6-methyl-7-anilinofluoran.

The compounds of this invention represented by Formula (I) are synthesized by a general method to be described below.

First, an m-aminophenol derivative (II) and phthalic anhydride (III) are subjected to condensation to synthesize a 2-(4'-amino-2'-hydroxybenzoyl)-benzoic acid derivative (IV) as shown schematically below.

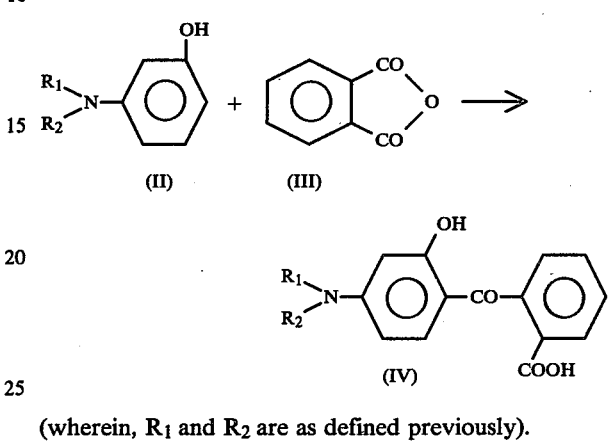

(wherein, $R_1$ and $R_2$ are as defined previously).

Then, the 2-(4'-amino-2'-hydroxybenzoyl)-benzoic acid derivative (IV) is caused to react with a diphenylamine derivative (V) of the following formula:

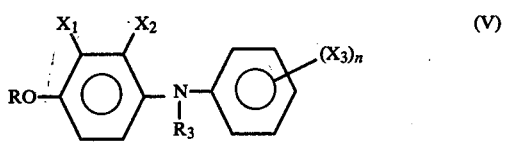

(wherein, $X_1$, $X_2$, $X_3$ and $R_3$ are as defined previously and R is selected from the group consisting of hydrogen atom, lower alkyl radicals of from one to four carbon atoms) by the medium of a dehydration condensing agent such as sulfuric acid or polyphosphoric acid at temperatures in the approximate range of from −10° C. to 100° C. for several hours to a few scores of hours. The fluoran compound represented by Formula (I) is obtained in the form of colorless crystals by pouring the reaction product into ice water, separating the precipitate consequently educed in the ice water, treating the precipitate with an alkali, separating the treated precipitate by filtration, drying it and recrystallizing it with an organic solvent.

While the colors which the fluoran derivatives represented by Formula (I) form upon contact with electron accepting substances are black to blackish green, the colors of blackish tone formed by the fluoran derivatives can be changed by mixing the fluoran derivatives with chromogens capable of forming colors of other tones. Otherwise, the colors of some other tones which are formed by certain chromogens can be changed by mixing these chromogens with the fluoran derivatives represented by Formula (I). Further, the fluoran derivatives can have their resistivity to light enhanced by mixing them with an ultraviolet ray absorbent, for example.

Effective use of these chromogens in pressure-sensitive copying sheets can be accomplished by following any one of the methods described in the specifications of U.S. Pat. Nos. 2,548,366, 2,800,458 and 2,969,370.

Application of the chromogens to heat-sensitive recording materials can be effected by any one of the methods described in Japanese Patent Publications Nos. 6040/1965, 4160/1968 and 14039/1970, for example.

These chromogenic substances are particularly suitable for use as pressure-sensitive copying (recording) substances. These substances embrace, for example, sheets which come in at least a paired form and which comprise at least one color-forming compound of Formula (I) or Supplementary Formula thereof enclosed in microcapsules rupturable under pressure and dissolved in an organic solvent and an electron-accepting substance. When this color-forming compound is brought into contact with the electron-accepting substance under pressure, it gives rise to a color at points at which the pressure is applied. Owing to its isolation from the electron-accepting substance, the color-forming compound contained in the pressure-sensitive substance is prevented from becoming activated. Generally, this isolation is accomplished by incorporating the color-forming compound in a structure of the form of foam, sponge or honeycomb. Preferably, the color-forming compound is entrapped by microcapsulation.

When the colorless color-forming compound of Formula (I) is dissolved in the organic solvent, it undergoes the process of microcapsulation and can be immediately used in the preparation of pressure-sensitive sheets. A colored image is obtained when the capsules are broken by the pressure such as from a pencil and, consequently, the color-forming compound solution passes into the adjoining sheet coated with a substrate capable of functioning as an electron-accepting substance. From the dye thus formed, there is obtained a color absorbed in the visible zone of electromagnetic spectrum.

Several characteristic techniques generally adopted for the preparation of microcapsules have long been known in the art. Methods well known for the purpose are described in the specifications of U.S. Pat. Nos. 2,183,053, 2,800,457, 2,800,458, 3,265,630, 2,964,331, 3,418,656, 3,418,250, 3,016,308, 3,424,827, 3,427,250, 3,405,071, 3,171,878 and 2,797,201, for example. Other methods are described in British Pat. No. 989,264 and particularly in British Pat. No. 1,156,725. These and other available methods are invariably suitable encapsulating color-forming compounds of the present invention.

Desirably the color-forming compounds of the present invention are dissolved in organic solvents when they are subjected to the encapsulation. The solvents are desired to be of an involatile type. Examples are polyhalogenated diphenyls such as trichlorodiphenyl and mixtures thereof with liquid paraffins, tricresyl phosphate, di-n-butyl phthalate, dioctyl phthalate, trichlorobenzene, nitrobenzene, trichloroethyl phosphate, petroleum ether, hydrocarbon oils such as paraffins, condensation derivatives of diphenyl or triphenyl, chlorinated or hydrogenated condensed aromatic hydrocarbons. Capsule walls are desirably obtained, as described in the specification of U.S. Pat. No. 2,800,457, for example, by coacervating a capsulating substance of gelatin uniformly on the surface of droplets of the color-forming compound solution.

Alternatively, these capsules may be desirably produced by the polycondensation of aminoplast or modified aminoplast as described in the specification of British Pat. Nos. 989,254 or 1,156,725.

The desirable arrangement is in a condition such that the enmicrocapsulated color-forming compound is deposited on the reverse side of the transfer sheet and the electron-accepting substance on the observe side of the receptor sheet.

The microcapsules may be contained in the lower coating of the upper sheet and the pigment reactor or electron acceptor and the coupler may be contained in the upper coating of the lower sheet. These components may otherwise be used in paper pulp. These methods are referred to as "chemical transfer" method.

Another arrangement is found in self-containing papers. In this particular arrangement, the microcapsules containing the color-forming compound and the pigment reactor are present in or on the same sheet as one or more individual coating or in paper pulp.

Such pressure-sensitive copying substances are dealt with in the specifications of U.S. Pat. Nos. 3,516,846, 2,730,457, 2,932,582, 3,427,180, 3,418,250 and 3,418,654. Other systems are shown in the specifications of British Pat. Nos. 1,042,597, 1,042,598, 1,042,596, 1,042,599, 1,053,935 and 1,517,650. The microcapsules containing color-forming compounds of Formula (I) are invariably suitable for these and other systems.

Desirably these capsules are fastened to their carriers with suitable adhesive agents. Since paper is a desirable substance for such carriers, substantially all paper coating agents such as, for example, gum arabic, polyvinyl alcohol, hydroxymethyl cellulose, casein, methyl cellulose and dextrin can be used as suitable adhesive agents.

The novel fluoran compounds can also be used as color-forming compounds in thermoreactive recording substances which are made up of at least a supporting element, a binder, a color-forming compound and an electron-accepting substance. A thermoreactive recording system comprises a heat-sensitive recording substance, a copying substance and paper. This system is used for recording information in an electronic computer, a teleprinter, a telewriter or a measuring instrument. Formation of record can also be effected by a hand holding therein a heated pen. Other means for guiding the recording initiated by heat is a laser beam. In another permissible arrangement of the thermoreactive recording substance, the color-forming compound may be dissolved or dispersed in the layer of binder and the color developing agent and the electron-accepting substance dissolved or dispersed in the binder of the second layer. Another possibility is that the color-forming compound and the color developing agent are both dispersed in one same layer. By the agency of heat, the binder is softened in the form of a figure in a specific zone and the dye is formed in the corresponding points. This is because the color-forming compound comes into contact with the electron-accepting substance at the points at which heat is applied.

The color developing agent is the same electron-accepting substance that is used on the pressure-sensitive paper. By reason of practicability, the color developing agent is required to be solid at normal room temperature and to melt or soften at temperatures above 50° C. Examples of products which satisfy this requirement include phenolic resins or phenolic compounds such as, for example, 4-tert-butyl phenol and 4-phenylphenol, 4-hydroxydiphenyl oxide, α-naphthol, 4-hydroxy-benzoic acid methyl ester, β-naphthol, 4-hydroxyacetophenone, 2,2'-dihydroxy-diphenyl, 4,4'-isopropylidenediphenol, 4,4'-isopropylidene-bis-(2-methyl phenol), 4,4'-bis-(hydroxyphenyl) valeric acid, hydroquinone, pyrogallol, phloroglucin, p-, m- or o-hydroxybenzoic acid, gallic acid, 1-hydroxy-2-naphthoic acid, boric acid and aliphatic dicarboxylic acids such as, for example, tartaric acid, oxalic acid, maleic acid, citraconic acid and succinic acid.

Desirably, there is used a binder of the type soluble and capable of forming film. This binder must be soluble in water. This is because fluoran compounds and color-developing agents are insoluble in water. This binder must be capable of being dispersed at normal room temperature so as to immobilize the color-forming compound and the color-developing agent. Thus, the two reactive components coexist in an uncombined state within the binder. Upon exposure to heat, the binder is softened or melted and brings the color-forming compound into contact with the color developing agent, giving rise to a color. In this case, the color developing agent may be any of the aforementioned co-reactors such as, for example, clay, phenolic resin or other phenolic compound.

The binder which is soluble in water or at least swellable in water is a hydrophilic polymer. Examples of such hydrophilic polymers include polyvinyl alcohol, polyacrylic acid, hydroxyethyl cellulose, methyl cellulose, carboxymethyl cellulose, polyacrylamide, polyvinyl pyrolidone, gelatin and starch.

Typical thermoreactive recording substances for which the color-forming compounds of the present invention can be used are described in the specifications of German Pat. No. 2,228,581, French Pat. No. 1,524,826, Swiss Pat. No. 407,185, German Pat. Application No. 2,110,854 and Swiss Pat. Nos. 164,976, 444,196 and 444,197.

EXAMPLES OF SYNTHESIS

1. Synthesis of 3-(N-methyl-N-n-amyl)-amino-6-methyl-7-anilinofluoran:

In 100 ml of concentrated sulfuric acid, 34.1 g of 2-[2'-hydroxy-4'-(N-methyl-N-n-amyl)-aminobenzoyl]-benzoic acid and 21.3 g of 2-methyl-4-methoxy-diphenylamine were dissolved at 30° C. and thereafter stirred at room temperature for 48 hours. After the reaction was completed, the reaction product was poured in 1000 g of ice water and the solid substance consequently precipitated therein was separated by filtration. The solid substance was disintegrated in water, alkalized with sodium hydroxide solution, then filtered and dried. The dried substance was then recrystallized from n-butyl alcohol to afford 34.3 g of a white solid product having a melting point of 173.5° to 176.5° C., which was identified to be 3-(N-methyl-N-n-amyl)-amino-6-methyl-7-anilinofluoran (of the structural formula shown below). This compound had its νmax in 95% acetic acid at 452 nm and 584 nm. The solution of this compound in toluene was free of color and, on contact with silica gel, instantaneously forms a color of blackish purple.

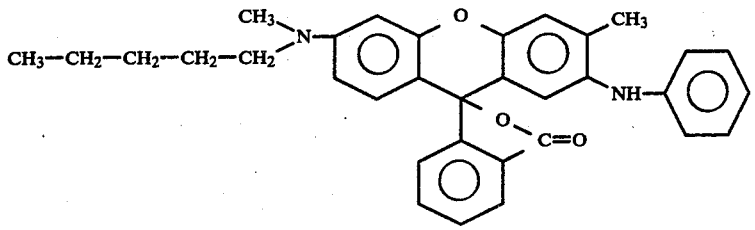

2. Synthesis of 3-(N-ethyl-N-n-amyl)-amino-6-methyl-7-anilinofluoran:

When the procedure of Synthesis 1 was repeated by using 2-[2'-hydroxy-4'-(N-ethyl-N-n-amyl)-aminobenzoyl]benzoic acid in place of 2-[2'-hydroxy-4'-(N-methyl-N-n-amyl)-aminobenzoyl]benzoic acid, there was obtained 30.5 g of a white solid substance having a melting point of 181° to 183.5° C. This compound was identified to be 3-(N-ethyl-N-n-amyl)-amino-6-methyl-7-anilinofluoran (of the structural formula shown below). This compound had its λmax in 95% acetic acid at 454 nm and 587 nm. The solution of this compound in toluene was free of color and, on contact with silica gel, instantaneously formed a color of blackish purple.

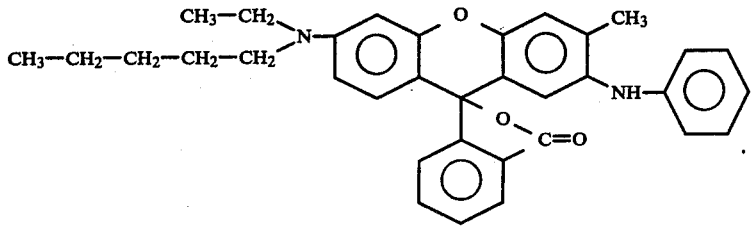

3. Synthesis of 3-(N-ethyl-N-n-amyl)-amino-6-methyl-7-(N-methyl-N-phenyl)-aminofluoran:

When the procedure of synthesis 1 was repeated by using 2-[2'-(hydroxy-4'-(N-ethyl-N-n-amyl)-aminobenzoyl]benzoic acid in place of 2-[2'-hydroxy-4'-(N-methyl-N-n-amyl)-aminobenzoyl]benzoic acid and 4-methoxy-N-methyl-diphenylamine in place of 2-methyl-4-methoxy-diphenylamine, there was obtained a white solid substance having a melting point of 121° to 123° C., which was identified to be 3-(N-ethyl-N-n-amyl)-amino-6-methyl-7-(N-methyl-N-phenylamino)-fluoran (of the structural formula shown below). The solution of this compound in toluene was free of color and, upon contact with silica gel, instantaneously formed a color of dark red.

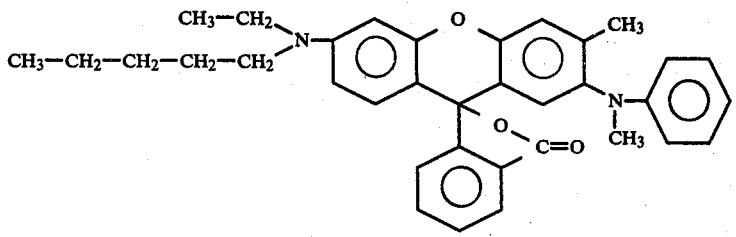

4. Synthesis of 3-(N-ethyl-N-n-amyl)-amino-7-(N-m-trifluoromethylphenyl)-aminofluoran:

When the procedure of Synthesis 1 was repeated by using 2-[2'-hydroxy-4'-(N-ethyl-N-n-amyl)-aminobenzoyl]benzoic acid in place of 2-[2'-hydroxy-4'-(N-methyl-N-n-amyl)-aminobenzoyl]benzoic acid and 4-methoxy-3'-trifluoromethyl diphenylamine in place of 2-methyl-4-methoxy-diphenylamine, there was obtained a white solid substance having a melting point of 118° to 121° C. The compound was identified to be 3-(N-ethyl-N-n-amyl)-amino-7-(N-m-trifluoromethylphenyl)-aminofluoran (of the structural formula shown below). This compound had its λmax in 95% acetic acid at 437 nm and 504 nm. The solution of this compound in toluene was free of color and, upon contact with silica gel, instantaneously formed a color of blackish purple.

6. Synthesis of 3-(N-ethyl-N-iso-amyl)-amino-6-methyl-7-anilinofluoran:

When the procedure of Synthesis 1 was repeated by using 2-[2'-hydroxy-4'-(N-ethyl-N-iso-amyl)-aminobenzoyl]benzoic acid in place of 2-[2'-hydroxy-4'-(N-methyl-N-n-amyl)-aminobenzoyl]benzoic acid, there was obtained a white solid substance having a melting point of 164° to 166.5° C. The compound was identified to be 3-(N-ethyl-N-iso-amyl)-amino-6-methyl-7-anilinofluoran (of the structural formula shown below). This compound had its λmax in 95% acetic acid at 454 nm and 588 nm. The solution of this compound in toluene was free of color and, upon contact with silica gel, instantaneously formed a color of blackish purple.

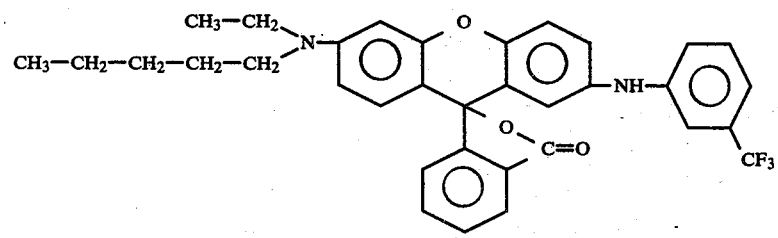

5. Synthesis of 3-(N-ethyl-N-n-amyl)-amino-5-methyl-7-(N-m-trifluoromethylphenyl)-aminofluoran:

When the procedure of Synthesis 1 was repeated by using 2-[2'-hydroxy-4'-(N-ethyl-N-n-amyl)-aminobenzoyl]benzoic acid in place of 2-[2'-hydroxy-4'-(N-methyl-N-n-amyl)-aminobenzoyl]benzoic acid and 3-methyl-4-methoxy-3'-trifluoromethyl diphenylamine in place of 2-methyl-4-methoxydiphenylamine, there was obtained a white solid substance having a melting point of 183.5° to 185.5° C. The compound was identified to be 3-(N-ethyl-N-n-amyl)-amino-5-methyl-7-(N-trifluoromethylphenyl)-aminofluoran (of the structural formula shown below). This compound has its λmax in 95% acetic acid at 437 nm and 586 nm. The solution of this compound in toluene was free of color and, upon contact with silica gel, instantaneously formed a color of blackish purple.

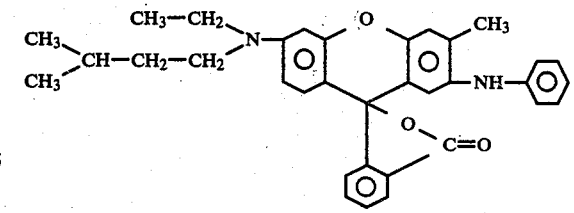

7. Synthesis of 3-(N-iso-amyl-N-n-hexyl)-amino-6-methyl-7-anilinofluoran:

When the procedure of Synthesis 1 was repeated by using 2-[2'-hydroxy-4'-(N-iso-amyl-N-n-hexyl)-aminobenzoyl]benzoic acid in place of 2-[2'-hydroxy-4'-(N-methyl-N-n-amyl)-aminobenzoyl]benzoic acid, there was obtained a white solid substance having a melting point of 102° to 105° C. The compound was

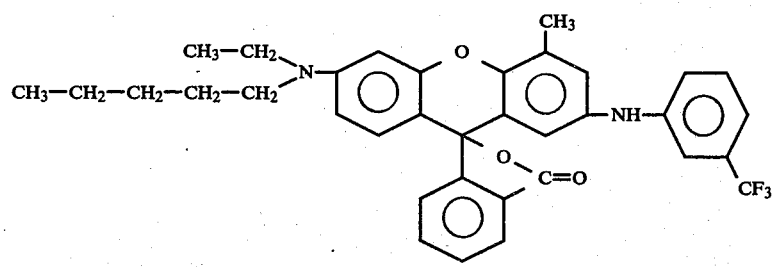

identified to be 3-(N-iso-amyl-N-n-hexyl)-amino-6-methyl-7-anilinofluoran (of the structural formula shown below). This compound had its λmax in 95% acetic acid at 455 nm and 589 nm. The solution of this compound in toluene was free of color and, upon contact with silica gel, instantaneously formed a color of blackish purple.

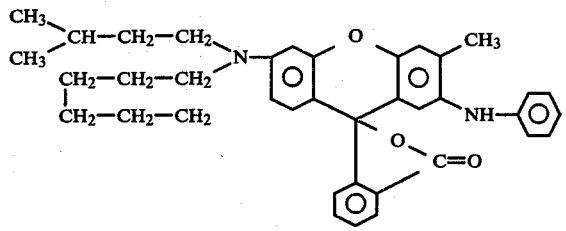

8. Synthesis of 3-(N-iso-amyl-N-n-hexyl)-amino-7-anilinofluoran:

When the procedure of Synthesis 1 was repeated by using 2-[2'-hydroxy-4'-(N-iso-amyl-N-n-hexyl)-aminobenzoyl]benzoic acid in place of 2-[2'-hydroxy-4'-(N-methyl-N-n-amyl)-aminobenzoyl]benzoic acid and 4-hydroxy diphenylamine in place of 2-methyl-4-methoxy-diphenylamine, there was obtained a white solid substance having a melting point of 145° to 147° C. The compound was identified to be 3-(N-iso-amyl-N-n-hexyl)-amino-7-anilinofluoran (of the structural formula shown below). This compound had its λmax in 95% acetic acid at 446 nm and 604 nm. The solution of this compound in toluene was free of color and, upon contact with silica gel, instantaneously formed a color of dark green.

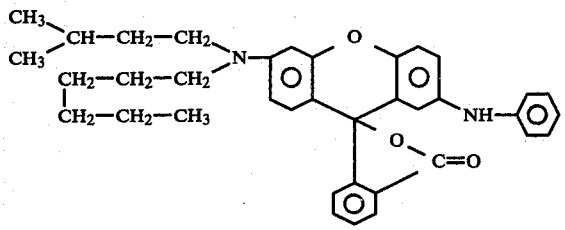

9. Synthesis of 3-(N-di-iso-amyl)-amino-6-methyl-7-anilinofluoran:

When the procedure of Synthesis 1 was repeated by using 2-(2'-hydroxy-4'-diiso-amylaminobenzoyl) benzoic acid in place of 2-[2'-hydroxy-4'-(N-methyl-N-n-amyl)-aminobenzoyl]benzoic acid, there was obtained a white solid substance having a melting point of 168° to 170° C. The compound was identified to be 3-(N-di-iso-amyl)-amino-6-methyl-7-anilinofluoran (of the structural formula shown below). This compound had its λmax in 95% acetic acid at 456 nm and 593 nm. The solution of this compound in toluene was free of color and, upon contact with silica gel, instantaneously formed a color of blackish purple.

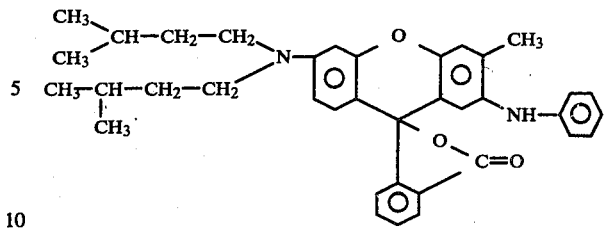

10. Synthesis of 3-(N-methyl-N-n-hexyl)-amino-6-methyl-7-anilinofluoran:

When the procedure of Synthesis 1 was repeated by using 2-[2'-hydroxy-4'-(N-methyl-N-n-hexyl)-aminobenzoyl]benzoic acid in place of 2-[2'-hydroxy-4'-(N-methyl-N-n-amyl)-aminobenzoyl]benzoic acid, there was obtained a white solid substance having a melting point of 154° to 156° C. The compound was identified to be 3-(N-methyl-N-n-hexyl)-amino-6-methyl-7-anilinofluoran (of the structural formula shown below). This compound had its λmax in 95% acetic acid at 453 nm and 587 nm. The solution of this compound in toluene was free of color and, upon contact with silica gel, instantaneously formed a color of blackish purple.

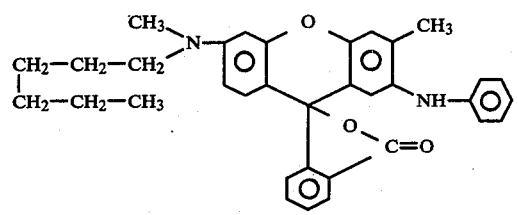

11. Synthesis of 3-(N-methyl-N-n-hexyl)-amino-7-anilinofluoran:

When the procedure of Synthesis 1 was repeated by using 2-[2'-hydroxy-4'-(N-methyl-N-n-hexyl)-aminobenzoyl]benzoic acid in place of 2-[2-hydroxy-4'-(N-methyl-N-n-amyl)-aminobenzoyl]benzoic acid and 4-methoxy diphenylamine in place of 2-methyl-4-methoxy-diphenylamine, there was obtained a white solid substance having a melting point of 134° to 137° C. The compound is identified to be 3-(N-methyl-N-n-hexyl)-amino-7-anilinofluoran (of the structural formula shown below). This compound had its λmax in 95% acetic acid at 444 nm and 602 nm. The solution of this compound in toluene was free of color and, upon contact with silica gel, instantaneously forms a color of dark green.

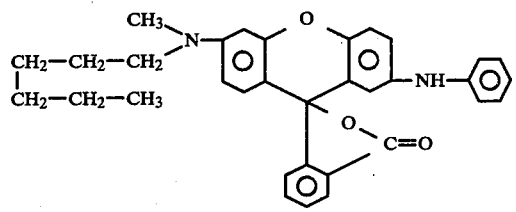

12. Synthesis of 3-(N-ethyl-N-n-hexyl)-amino-6-methyl-7-anilinofluoran:

When the procedure of Synthesis 1 was repeated by using 2-[2'-hydroxy-4'-(N-ethyl-N-n-hexyl)-aminobenzoyl]-benzoic acid in place of 2-[2'-hydroxy-4'-(N-methyl-N-n-amyl)-aminobenzoyl]benzoic acid, there was obtained a white solid substance having a melting point of 145° to 148° C. The compound was identified to be 3-(N-ethyl-N-n-hexyl)-amino-6-methyl-7-anilinofluoran (of the structural formula shown below). This compound had its λmax in 95% acetic acid at 453 nm and 587 nm. The solution of this compound in toluene was free of color and, upon contact with silica gel, instantaneously formed a color of blackish purple.

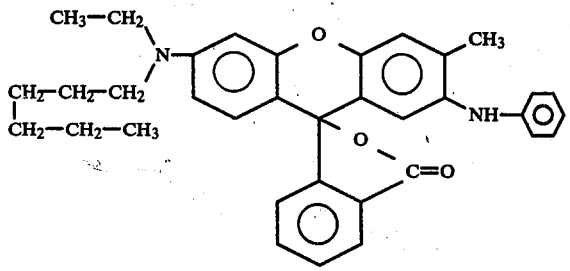

13. Synthesis of 3-(N-ethyl-N-n-hexyl)-amino-7-anilinofluoran:

When the procedure of Synthesis 1 was repeated by using 2-[2'-hydroxy-4'-(N-ethyl-N-n-hexyl)-aminobenzoyl]benzoic acid in place of 2-[2'-hydroxy-4'-(N-methyl-N-n-amyl)-aminobenzoyl]benzoic acid and 4-methoxy diphenylamine in place of 2-methyl-4-methoxy-diphenylamine, there was obtained a white solid substance having a melting point of 170° to 172° C. The compound was identified to be 3-(N-ethyl-N-n-hexyl)-amino-7-anilinofluoran (of the structural formula shown below). This compound had its λmax in 95% acetic acid at 446 nm and 601 nm. The solution of this compound in toluene was free of color and, upon contact with silica gel, instantaneously formed a color of dark green.

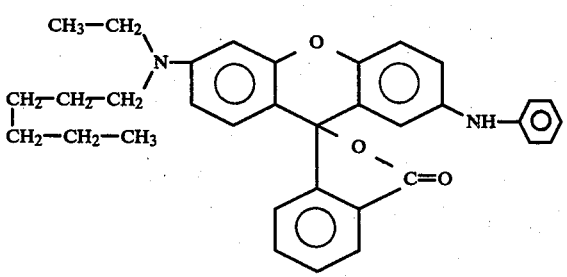

14. Synthesis of 3-(N-ethyl-N-n-hexyl)-amino-7-(N-m-tolyl)-aminofluoran:

When the procedure of Synthesis 1 was repeated by using 2-[2'-hydroxy-4'-(N-ethyl-N-n-hexyl)-aminobenzoyl]benzoic acid in place of 2-[2'-hydroxy-4'-(N-methyl-N-n-amyl)-aminobenzoyl]benzoic acid and 4-methoxy-3'-methyl diphenylamine in place of 2-methyl-4-methoxy-diphenylamine, there was obtained a white solid substance having a melting point of 145° to 147° C. The compound was identified to be 3-(N-ethyl-N-n-hexyl)-amino-7-(N-m-tolyl)-aminofluoran (of the structural formula shown below). This compound had its λmax in 95% acetic acid at 446 nm and 605 nm. The solution of this compound in toluene was free of color and, upon contact with silica gel, instantaneously formed a color of dark green.

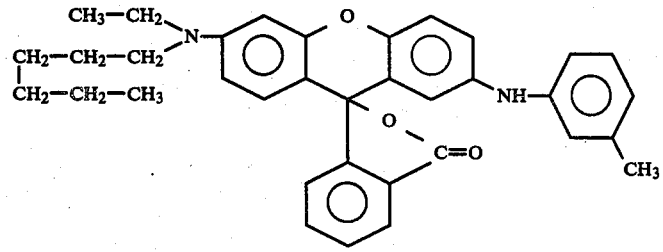

15. Synthesis of 3-(N-ethyl-N-n-hexyl)-amino-7-(N-methyl-N-phenyl)-aminofluoran:

When the procedure of Synthesis 1 was repeated by using 2-[2'-hydroxy-4'-(N-ethyl-N-n-hexyl)-aminobenzoyl]benzoic acid in place of 2-[2'-hydroxy-4'-(N-methyl-N-n-amyl)-aminobenzoyl]benzoic acid and 4-methoxy-N-methyl diphenylamine in place of 2-methyl-4-methoxy-diphenylamine, there was obtained a white solid substance having a melting point of 127° to 130° C. The compound was identified to be 3-(N-ethyl-N-n-hexyl)-amino-7-(N-methyl-N-phenyl)-aminofluoran (of the structural formula shown below). This compound had its λmax in 95% acetic acid at 442 nm and 600 nm. The solution of this compound in toluene was free of color and, upon contact with silica gel, instantaneously formed a color of dark green.

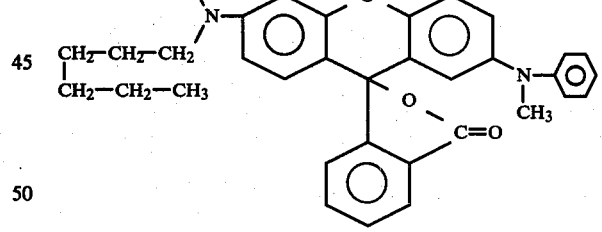

16. Synthesis of 3-(N-ethyl-N-n-hexyl)-amino-7-(N-methyl-N-p-tolyl)-aminofluoran:

When the procedure of Synthesis 1 was repeated by using 2-[2'-hydroxy-4'-(N-ethyl-N-n-hexyl)-aminobenzoyl]benzoic acid in place of 2-[2'-hydroxy-4'-(N-methyl-N-n-amyl)-aminobenzoyl]benzoic acid and 4-methoxy-4'-N-dimethyl diphenylamine in place of 2-methyl-4-methoxy-diphenylamine, there was obtained a white solid substance having a melting point of 146° to 149° C. The compound was identified to be 3-(N-ethyl-N-n-hexyl)-amino-7-(N-methyl-N-p-tolyl)-aminofluoran (of the structural formula shown below). The compound had its λmax in 95% acetic acid at 444 nm and 605 nm. The solution of this compound in toluene was free of color and, upon contact with silica gel, instantaneously formed a color of dark green.

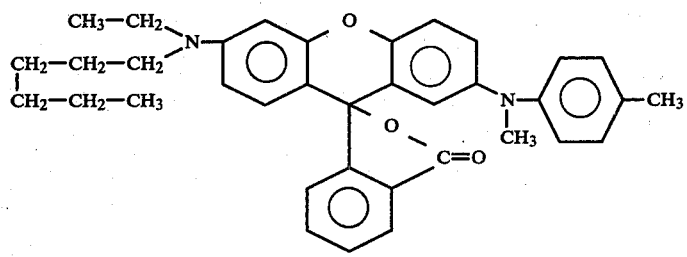

17. Synthesis of 3-(N-ethyl-N-n-hexyl)-amino-6-methyl-7-(N-p-tolyl)-aminofluoran:

When the procedure of Synthesis 1 was repeated by using 2-[2'-hydroxy-4'-(N-ethyl-N-n-hexyl)-aminobenzoyl]benzoic acid in place of 2-[2'-hydroxy-4'-(N-methyl-N-n-amyl)-aminobenzoyl]benzoic acid and 2,4'-dimethyl-4-methoxy diphenylamine in place of 2-methyl-4-methoxy-diphenylamine, there was obtained a white solid substance having a melting point of 150° to 152° C. The compound was identified to be 3-(N-ethyl-N-n-hexyl)-amino-6-methyl-7-(N-p-tolyl)-aminofluoran (of the structural formula shown below). This compound had its λmax in 95% acetic acid at 452 nm and 597 nm. The solution of this compound in toluene was free of color and, upon contact with silica gel, instantaneously formed a color of black.

contact with silica gel, instantaneously formed a color of blackish purple.

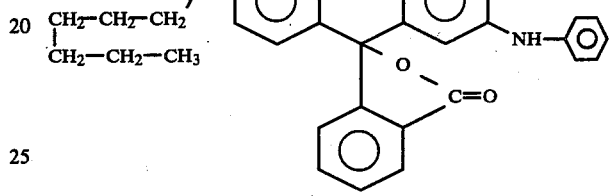

19. Synthesis of 3-(N-ethyl-N-n-hexyl)-amino-6-ethyl-7-(N-p-tolyl)-aminofluoran:

When the procedure of Synthesis 1 was repeated by using 2-[2'-hydroxy-4'-(N-ethyl-N-n-hexyl)-aminobenzoyl]benzoic acid in place of 2-[2'-hydroxy-4'-(N-methyl-N-n-amyl)-aminobenzoyl]benzoic acid and 2-ethyl-4-methoxy-4'-methyl diphenylamine in place of 2-methyl-4-methoxy-diphenylamine, there was obtained a white solid substance having a melting point of 160.5° to 162° C. The compound was identified to be 3-(N-ethyl-N-n-hexyl)-amino-6-ethyl-7-(N-p-tolyl)-aminofluoran (of the structural formula shown below). This compound had its λmax in 95% acetic acid at 455 nm and 596 nm. The solution of this compound in toluene was free of color and, upon contact with silica gel, instantaneously formed a color of black.

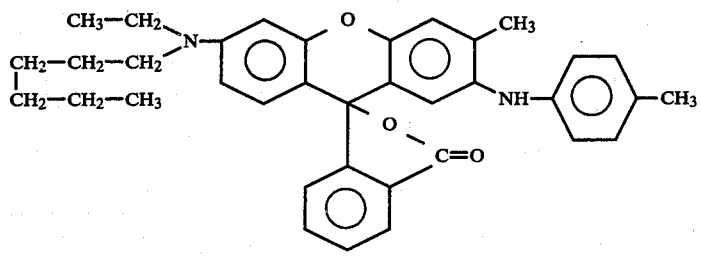

18. Synthesis of 3-(N-ethyl-N-n-hexyl)-amino-6-ethyl-7-anilinofluoran:

When the procedure of Synthesis 1 was repeated by using 2-[2'-hydroxy-4'-(N-ethyl-N-n-hexyl)-aminobenzoyl]benzoic acid in place of 2-[2'-hydroxy-4'-(N-methyl-N-n-amyl)-aminobenzoyl]benzoic acid and 2-ethyl-4-methoxy diphenylamine in place of 2-methyl-4-methoxy-diphenylamine, there was obtained a white solid substance having a melting point of 114° to 116° C. The compound was identified to be 3-(N-ethyl-N-n-hexyl)-amino-6-ethyl-7-anilinofluoran (of the structural formula shown below). This compound had its λmax in 95% acetic acid at 455 nm and 589 nm. The solution of this compound in toluene was free of color and, upon

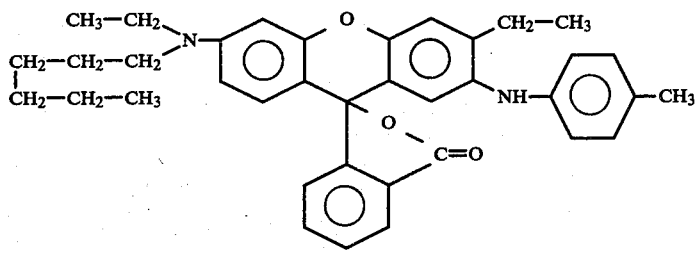

20. Synthesis of 3-(N-ethyl-N-n-hexyl)-amino-7-(N-n-butyl-N-phenyl)-aminofluoran:

When the procedure of Synthesis 1 was repeated by using 2-[2'-hydroxy-4'-(N-ethyl-N-n-hexyl)-aminobenzoyl]benzoic acid in place of 2-[2'-hydroxy-4'-N-methyl-N-n-amyl)-aminobenzoyl]benzoic acid and 4-methoxy-N-n-butyl diphenylamine in place of 2-methyl-4-methoxy-diphenylamine, there was obtained a white solid substance. The compound was identified to be 3-(N-ethyl-N-n-hexyl)-amino-7-(N-n-butyl-N-phenyl)-aminofluoran (of the structual formula shown below). This compound had its λmax in 95% acetic acid at 441 nm and 603 nm. The solution of this compound in toluene was free of color and, upon contact with silica gel, instantaneously formed a color of dark green.

22. Synthesis of 3-(N-ethyl-N-β-ethylhexyl)-amino-6-methyl 7-anilinofluoran:

When the procedure of Synthesis 1 was repeated by using 2-[2'-hydroxy-4'-(N-ethyl-N-β-ethylhexyl)-aminobenzoyl]benzoic acid in place of 2-[2'-hydroxy-4'-(N-methyl-N-n-amyl)-aminobenzoyl]benzoic acid, there was obtained a white solid substance having a melting point of 136° to 139° C. The compound was identified to be 3-(N-ethyl-N-β-ethylhexyl)-amino-6-methyl-7-anilinofluoran (of the structural formula shown below). This compound had its λmax in 95% acetic acid at 455 nm and 589 nm. The solution of this compound in toluene was free of color and, upon contact with silica gel, instantaneously formed a color of blackish purple.

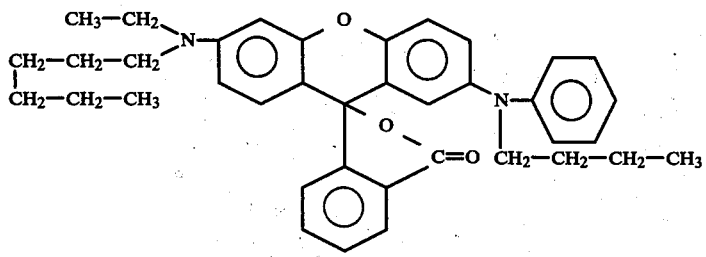

21. Synthesis of 3-(N-methyl-N-β-ethylhexyl)-amino-6-methyl-7-anilinofluoran:

When the procedure of Synthesis 1 was repeated by using 2-[2'-hydroxy-4'-(N-methyl-N-β-ethylhexyl)-aminobenzoyl]benzoic acid in place of 2-[2'-hydroxy-4'-(N-methyl-N-n-amyl)-aminobenzoyl]benzoic acid, there was obtained a white solid substance having a melting point of 91° to 93° C. The compound was identified to be 3-(N-methyl-N-β-ethylhexyl)-amino-6-methyl-7-anilinofluoran (of the structural formula shown below). This compound had its λmax in 95% acetic acid at 456 nm and 589 nm. The solution of this compound in toluene was free of color and, upon contact with silica gel, instantaneously formed a color of blackish purple.

23. Synthesis of 3-(N-ethyl-N-β-ethylhexyl)-amino-7-anilinofluoran:

When the procedure of Synthesis 1 was repeated by using 2-[2'-hydroxy-4'-(N-ethyl-N-β-ethylhexyl)-aminobenzoyl]benzoic acid in place of 2-[2'-hydroxy-4'-(N-methyl-N-n-amyl)-aminobenzoyl]benzoic acid and 4-methoxy diphenylamine in place of 2-methyl-4-methoxy-diphenylamine, there was obtained a white solid substance having a melting point of 136° to 139° C. The compound was identified to be 3-(N-ethyl-N-β-ethylhexyl)-amino-7-anilinofluoran (of the structural formula shown below). This compound had its λmax in 95% acetic acid at 447 nm and 605 nm. The solution of this compound in toluene was free of color and, upon contact with silica gel, instantaneously formed a color of dark green.

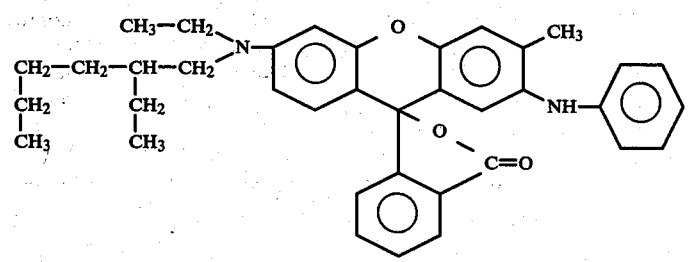

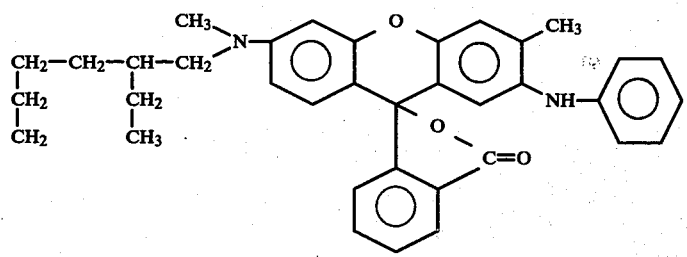

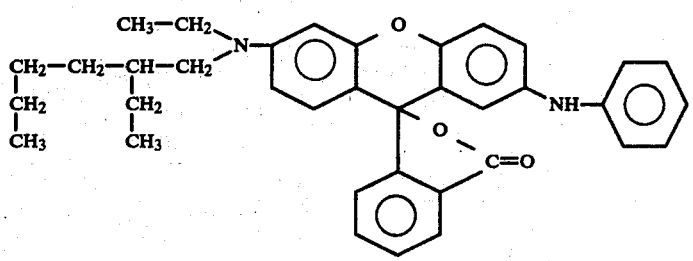

24. Synthesis of 3-(N-methyl-N-β-ethylhexyl)-amino-7-anilinofluoran:

When the procedure of Synthesis 1 was repeated by using 2-[2'-hydroxy-4'-(N-methyl-N-β-ethylhexyl)-aminobenzoyl]benzoic acid in place of 2-[2'-hydroxy-4'-(N-methyl-N-n-amyl)-aminobenzoyl]benzoic acid and 4-methoxy diphenylamine in place of 2-methyl-4-methoxy-diphenylamine, there was obtained a white solid substance having a melting point of 135° to 138° C. The compound was identified to be 3-(N-methyl-N-β-ethylhexyl)-amino-7-anilinofluoran (of the structural formula shown below). This compound had its λmax in 95% acetic acid at 446 nm and 602 nm. The solution of this compound in toluene is free of color and, upon contact with silica gel, instantaneously formed a color of dark green.

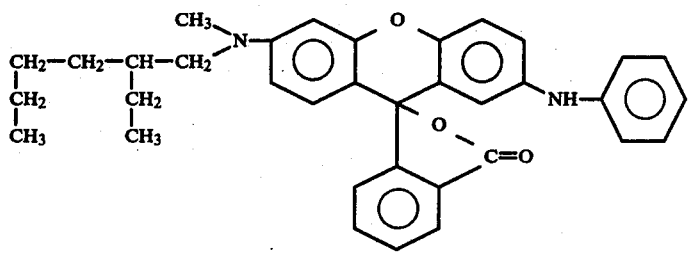

As shown in the subsequent tables, similar fluoran compounds were obtained by using varying raw materials indicated in place of 2-[2'-hydroxy-4'-(N-methyl-N-n-amyl)-aminobenzoyl]benzoic acid and 2-methyl-4-methoxy-diphenylamine. The solutions of these compounds in toluene invariably were free of color and, upon contact with silica gel, rapidly form colors of indicated hues.

| Example No. | Benzoyl-benzoic acid | Diphenylamine | Product | Hue |
|---|---|---|---|---|
| 25 | 4-[N-methyl-N-(n-pentyl)amino]-2-hydroxy-2'-carboxybenzophenone | 4-methoxy-2-methyl-4'-methyldiphenylamine | corresponding fluoran | Black |
| 26 | 4-[N-methyl-N-(n-pentyl)amino]-2-hydroxy-2'-carboxybenzophenone | 4-methoxy-3-methyl-3'-chlorodiphenylamine | corresponding fluoran | Dark green |
| 27 | 4-[N-methyl-N-(n-pentyl)amino]-2-hydroxy-2'-carboxybenzophenone | 4-methoxy-3-methyl-2',5'-dimethyldiphenylamine | corresponding fluoran | Dark green |

-continued

| Example No. | Benzoyl-benzoic acid | Diphenylamine | Product | Hue |
|---|---|---|---|---|
| 28 | | | | Black |
| 29 | | | | Dark green |
| 30 | | | | Blackish purple |

-continued

| Example No. | Benzoyl-benzoic acid | Diphenylamine | Product | Hue |
|---|---|---|---|---|
| 31 | (structure) | (structure) | (structure) | Black |
| 32 | (structure) | (structure) | (structure) | Dark green |
| 33 | (structure) | (structure) | (structure) | Blackish purple |

-continued

| Example No. | Benzoyl-benzoic acid | Diphenylamine | Product | Hue |
|---|---|---|---|---|
| 34 | [structure: 2-(2-hydroxy-4-(N-butyl-N-isoamyl)aminobenzoyl)benzoic acid] | [structure: 4-methoxy-3-methyl-4'-methyldiphenylamine] | [fluoran structure with N(CH₂(CH₂)₂CH₃)(CH₂CH(CH₃)CH₂CH₃), CH₃, and NH-C₆H₄-CH₃ substituents] | Dark green |
| 35 | [structure: 2-(2-hydroxy-4-di-n-butylaminobenzoyl)benzoic acid] | [structure: 4-methoxy-3-methyl-4'-methyldiphenylamine] | [fluoran structure with N(CH₂(CH₂)₃CH₃)₂, CH₃, and NH-C₆H₅ substituents] | Blackish purple |
| 36 | [structure: 2-(2-hydroxy-4-di-n-butylaminobenzoyl)benzoic acid] | [structure: 4-methoxy-3-methyl-2',4'-dichlorodiphenylamine] | [fluoran structure with N(CH₂(CH₂)₃CH₃)₂, CH₃, and NH-C₆H₃Cl₂ substituents] | Blackish purple |

-continued

| Example No. | Benzoyl-benzoic acid | Diphenylamine | Product | Hue |
|---|---|---|---|---|
| 37 | 2-[2-hydroxy-4-(N-isobutyl-N-isopentyl)amino-benzoyl]benzoic acid | 4-ethoxy-2-methyl-4'-methyl-diphenylamine | Corresponding fluoran with N-isobutyl-N-isopentylamino group, 3'-methyl-4'-(p-tolyl)amino substitution | Black |
| 38 | 2-[2-hydroxy-4-(N-ethyl-N-hexyl)amino-benzoyl]benzoic acid | 4-methoxy-2'-chloro-diphenylamine | Corresponding fluoran with N-ethyl-N-hexylamino group, 4'-(2-chlorophenyl)amino substitution | Blackish purple |
| 39 | 2-[2-hydroxy-4-(N-ethyl-N-hexyl)amino-benzoyl]benzoic acid | 4-hydroxy-2-methyl-diphenylamine | Corresponding fluoran with N-ethyl-N-hexylamino group, 3'-methyl-4'-phenylamino substitution | Blackish purple |

-continued

| Example No. | Benzoyl-benzoic acid | Diphenylamine | Product | Hue |
|---|---|---|---|---|
| 40 | [structure with OH, COOH, N(CH₂CH₂CH₃)(CH₂(CH₂)₄CH₃)] | 4-methoxy-4'-bromo diphenylamine (OCH₃ ... NH ... Br) | [xanthene-type structure with Br-phenyl-NH, N(CH₂CH₂CH₃)(CH₂(CH₂)₄CH₃)] | Dark green |
| 41 | [structure with OH, COOH, N(CH₃(CH₂)₄CH₂)₂] | 4-methoxy diphenylamine (OCH₃ ... NH ... phenyl) | [xanthene-type structure with phenyl-NH, N(CH₃(CH₂)₄CH₂)₂] | Dark green |
| 42 | [structure with OH, COOH, N(CH₃(CH₂)₄CH₂)₂] | 2-methyl-4-methoxy diphenylamine (OCH₃, CH₃ ... NH ... phenyl) | [xanthene-type structure with CH₃, phenyl-NH, N(CH₃(CH₂)₄CH₂)₂] | Blackish purple |

-continued

| Example No. | Benzoyl-benzoic acid | Diphenylamine | Product | Hue |
|---|---|---|---|---|
| 43 | structure with OH, COO, COOH, N(CH₃)(CH₂(CH₂)₅CH₃) | 4-methoxy-N-phenylaniline (OCH₃-C₆H₄-NH-C₆H₅) | xanthene dye with NHPh, OCH₃, N(CH₃)(CH₂(CH₂)₅CH₃) | Dark green |
| 44 | structure with OH, COO, COOH, N(CH₃)(CH₂(CH₂)₅CH₃) | 2-methyl-4-methoxy-N-phenylaniline | xanthene dye with NHPh, CH₃, N(CH₃)(CH₂(CH₂)₅CH₃) | Blackish purple |
| 45 | structure with OH, COO, COOH, N(CH₂CH₃)(CH₂(CH₂)₅CH₃) | 4-methoxy-N-phenylaniline | xanthene dye with NHPh, N(CH₂CH₃)(CH₂(CH₂)₅CH₃) | Dark green |

-continued

| Example No. | Benzoyl-benzoic acid | Diphenylamine | Product | Hue |
|---|---|---|---|---|
| 46 | (structure with OH, COOH, and N(CH₂CH₃)(CH₂(CH₂)₅CH₃)) | 4-methoxy-2-methyl-N-phenylaniline (OCH₃, CH₃, NH-phenyl) | Fluoran structure with CH₃, NH-phenyl, O-C=O lactone, and N(CH₂CH₃)(CH₂(CH₂)₅CH₃) | Blackish purple |
| 47 | (structure with OH, COOH, and N(CH₃)(CH₂(CH₂)₆CH₃)) | 4-methoxy-N-phenylaniline (OCH₃, NH-phenyl) | Fluoran structure with CH₃, NH-phenyl, O-C=O lactone, and N(CH₃)(CH₂(CH₂)₆CH₃) | Dark green |
| 48 | (structure with OH, COOH, and N(CH₂(CH₂)₆CH₃)₂) | 4-methoxy-2-methyl-N-phenylaniline (OCH₃, CH₃, NH-phenyl) | Fluoran structure with CH₃, NH-phenyl, O-C=O lactone, and N(CH₂(CH₂)₆CH₃)₂ | Blackish purple |

-continued

| Example No. | Benzoyl-benzoic acid | Diphenylamine | Product | Hue |
|---|---|---|---|---|
| 49 | 2-(2-hydroxy-4-(N-ethyl-N-n-octyl)aminobenzoyl)benzoic acid | 4-methoxydiphenylamine | corresponding fluoran with CH₃—CH₂ and CH₃—(CH₂)₆—CH₂ on N, and NH—phenyl | Dark green |
| 50 | 2-(2-hydroxy-4-(N-methyl-N-isoamyl)aminobenzoyl)benzoic acid | 2-methyl-4-methoxy-4'-methyldiphenylamine | corresponding fluoran | — |
| 51 | 2-(2-hydroxy-4-(N-ethyl-N-isoamyl)aminobenzoyl)benzoic acid | 2-methyl-4-methoxy-4'-methyldiphenylamine | corresponding fluoran | Black |

-continued

| Example No. | Benzoyl-benzoic acid | Diphenylamine | Product | Hue |
|---|---|---|---|---|
| 52 | 2-hydroxy-4-(N-methyl-N-n-hexylamino)benzoyl benzoic acid | 4-methoxy-2-methyl-4'-methyl diphenylamine | (cyclohexyl-fused lactone product with N(CH₃)(n-C₆H₁₁) and NH-C₆H₄-CH₃ substituents) | Black |
| 53 | 2-hydroxy-4-(N,N-di-n-octylamino)benzoyl benzoic acid | 4-methoxy-N-methyl diphenylamine | (phthalide product with N(n-C₈H₁₇)₂ and N(CH₃)(C₆H₅) substituents) | Dark green |

Examples of Comparative Test

The compounds of this invention and corresponding compounds of prior art were subjected to a comparative test with respect to the aforementioned characteristics, a through d.

List of Known Compounds Used as Comparison

A; 3-diethylamino-6-methyl-7-anilinofluoran
B; 3-diethylamino-6-ethyl-7-anilinofluoran
C; 3-diethylamino-6-methyl-7-(N-p-tolyl)-aminofluoran
D; 3-diethylamino-6-ethyl-7-(N-p-tolyl)-aminofluoran
E; 3-(N-ethyl-N-benzyl)-amino-6-methyl-7-anilinofluoran
F; 3-diethylamino-7-(N-m-triluoromethylphenyl)-aminofluoran
G; 3-diethylamino-5-methyl-7-(N-m-trifluoromethylphenyl)-aminofluoran
H; 3-(N-ethyl-N-p-tolyl)-amino-6-methyl-7-anilinofluoran
I; 3-(N-methyl-N-cyclohexyl)-amino-6-methyl-7-anilinofluoran
J; 3-diethylamino-7-(N-m-tolyl)-aminofluoran
K; 3-diethylamino-7-anilinofluoran
L; 3-diethylamino-7-(N-methyl-N-phenyl)-aminofluoran
M; 3-diethylamino-7-(N-methyl-N-p-tolyl)-aminofluoran
N; 3-(N-methyl-N-cyclohexyl)-amino-7-anilinofluoran
O; 3-diethylamino-7-(N-benzyl-N-phenyl)-aminofluoran
P; 3-diethylamino-6-methyl-7-(N-methyl-N-phenyl)-aminofluoran a. Spontaneous color forming property in dilute aqueous acid solutions:

A 3% toluene solution of a varying fluoran compound (15 ml) and an aqueous 15% acetic acid solution (10.5 ml) were shaken vigorously for one minute and the resultant mixture was left to stand at rest. The colored aqueous solution of acetic acid was tested colorimetrically with Shimadzu spectrophotometer. The results are shown in Table 1 below.

TABLE 1

| | PRESENT COMPOUND | | | KNOWN COMPOUND | |
|---|---|---|---|---|---|
| Example No. of Synthesis | Maximum Absorption Wavelength (nm) | Absorbancy | | Maximum Absorption Wavelength (nm) | Absorbancy |
| 1 | 535 | 0.180 | A | 570 | 1.11 |
| 2 | 535 | 0.188 | | | |
| 6 | 540 | 0.140 | | | |
| 7 | 570 | 0.100 | | | |
| 9 | 575 | 0.115 | | | |
| 10 | 564 | 0.181 | | | |
| 12 | 550 | 0.139 | | | |
| 21 | 553 | 0.152 | | | |
| 22 | 550 | 0.060 | | | |
| 50 | 550 | 0.130 | | | |
| 48 | 553 | 0.090 | | | |
| 18 | 550 | 0.060 | B | 555 | 1.570 |
| 17 | 550 | 0.030 | C | 548 | 0.585 |
| 51 | 540 | 0.163 | | | |
| 52 | 540 | 0.100 | | | |
| 19 | 550 | 0.025 | D | 550 | 0.400 |

The results indicate that the fluoran compounds of the present invention have very low degrees of solubility in dilute acids as compared with fluoran compounds of prior art. This fact implies that when the aqueous solution of gelatin is coagulated with a dilute acid in the preparation of microcapsules for use in the pressure-sensitive copying sheets, the fluoran compound of this invention has little possibility of coloring the solution.

b. Solubility in organic solvent:

A varying compound was tested for its solubility at 25° C. in Hisol SAS (diaryl ethane type solvent made by Nihon Sekiyu K.K. for use in pressure-sensitive copying sheets) and in toluene. The results are shown in Table 2 below.

TABLE 2

| PRESENT COMPOUND | | | KNOWN COMPOUND | | |
|---|---|---|---|---|---|
| Example No. of Synthesis | Hisol SAS (%) | Toluene (%) | | Hisol SAS (%) | Toluene (%) |
| 1 | 9.1 | 8.0 | A | 1.2 | 8.0 |
| 2 | 8.7 | 8.0 | | | |
| 6 | 3.5 | 16.5 | | | |
| 7 | above 20 | above 40 | | | |
| 9 | above 15 | above 40 | | | |
| 10 | 5 | 10 | | | |
| 12 | 3.1 | 16.0 | | | |
| 21 | above 20 | above 40 | | | |
| 22 | above 20 | above 40 | | | |
| 50 | 15.9 | 18.2 | | | |
| 48 | 10.2 | 40.3 | | | |
| 18 | above 25 | above 60 | B | above 25 | above 60 |
| 17 | 16.5 | 8.2 | C | 2.4 | 2.7 |
| 51 | 3.2 | 6.1 | | | |
| 52 | 15.0 | 25.0 | | | |
| 19 | 10 | 11 | D | 8.6 | 9.1 |
| — | — | — | E | 8.1 | 6.1 |
| 4 | above 15 | above 30 | F | 4.0 | 6.8 |
| 5 | 5.0 | 6.0 | G | 4.1 | 5.3 |
| — | — | — | H | 0.9 | 2.3 |
| — | — | — | I | 5.5 | 4.5 |
| 14 | 13.3 | 18.9 | J | 10.3 | 8.2 |
| 8 | 11.4 | 48.0 | K | 2.6 | 1.6 |
| 11 | 14.0 | 6.4 | | | |
| 13 | 4.9 | 7.9 | | | |
| 23 | above 20 | above 20 | | | |
| 24 | above 20 | above 20 | | | |
| 15 | 16.9 | 42.6 | L | 11.9 | 10.0 |
| 53 | 30 | 30 | | | |
| 16 | above 20 | above 40 | M | 8.7 | 5.5 |
| — | — | — | N | 8.8 | 6.6 |
| — | — | — | O | 8.8 | 13.0 |
| 3 | above 20 | above 40 | P | above 20 | above 20 |

It is clear from the table that the compounds of this invention excel in solubility in organic solvents. This fact proves that the compounds have no possibility of being educed in the form of crystals inside microcapsules during the manufacture of pressure-sensitive copying sheets and that in the process of microcapsulation, they accomplish the economy of saving the consumption of expensive aromatic solvents by an increased consumption of relatively less expensive petroleum solvents.

c. Spontaneous color forming property exhibited upon application to heat-sensitive sheets:

In accordance with the method disclosed in Japanese Patent Publication No. 14039/1970, a varying fluoran compound was finely divided in conjunction with an aqueous PVA solution and then mixed such as with bisphenol A to prepare a coating material for application to heat-sensitive recording sheets. Already at this stage, coating materials using fluoran compounds of prior art developed green to black colors by themselves and, as a natural consequence, heat-sensitive recording sheets coated with these materials had their textures colored. Then, the sheets thus produced were tested for surface condition by means of Macbeth Reflection Densitometer using WRATTEN filter #106. The results are shown in Table 3.

TABLE 3

| PRESENT COMPOUND | | KNOWN COMPOUND | |
|---|---|---|---|
| Example No. of Synthesis | Color Density | | Color Density |
| 1 | 0.09 | A | 0.18 |
| 2 | 0.08 | | |
| 6 | 0.10 | | |
| 7 | 0.09 | | |
| 9 | 0.12 | | |
| 10 | 0.10 | | |
| 12 | 0.09 | | |
| 21 | 0.13 | | |
| 22 | 0.11 | | |
| 50 | 0.11 | | |
| 48 | 0.06 | | |
| 18 | 0.08 | B | 0.25 |
| 17 | 0.08 | C | 0.20 |
| 51 | 0.09 | | |
| 52 | 0.11 | | |
| 19 | 0.08 | D | 0.22 |

It is clear from Table 3 that heat-sensitive recording sheets produced by using fluoran compounds of the present invention experience less coloration of texture and enjoy higher utility than those produced by using fluoran compounds of prior art.

d. Thermal sensitivity exhibited upon application to heat-sensitive sheets:

The heat-sensitive recording sheets prepared as described in the preceding paragraph "C" were tested for color-forming concentration by means of Macbeth Reflection Densitometer using WRATTEN filter #106, with the test temperature varied and the test time fixed. The test conditions were one second of heat application time and 1.5 kg/cm² of pressure. The results are shown in Table 4.

TABLE 4

| Example No. of Synthesis | PRESENT COMPOUND Temperature (°C.) | | | | | | KNOWN COMPOUND Temperature (°C.) | | | | | | |
|---|---|---|---|---|---|---|---|---|---|---|---|---|---|
| | 90 | 100 | 110 | 130 | 150 | 170 | | 90 | 100 | 110 | 130 | 150 | 170 |
| 1 | 0.10 | 0.13 | 0.20 | 0.72 | 1.15 | 1.20 | A | 0.15 | 0.18 | 0.20 | 0.54 | 1.04 | 1.14 |
| 2 | 0.09 | 0.10 | 0.15 | 0.58 | 1.10 | 1.19 | | | | | | | |
| 6 | 0.10 | 0.13 | 0.25 | 0.75 | 1.18 | 1.20 | | | | | | | |
| 7 | 0.13 | 0.28 | 0.46 | 0.68 | 1.05 | 1.10 | | | | | | | |
| 9 | 0.13 | 0.15 | 0.25 | 0.76 | 1.21 | 1.22 | | | | | | | |
| 10 | 0.10 | 0.12 | 0.19 | 0.80 | 1.18 | 1.20 | | | | | | | |
| 12 | 0.09 | 0.11 | 0.23 | 0.90 | 1.15 | 1.20 | | | | | | | |
| 21 | 0.15 | 0.23 | 0.55 | 0.95 | 1.14 | 1.14 | | | | | | | |
| 22 | 0.11 | 0.14 | 0.33 | 0.88 | 1.18 | 1.20 | | | | | | | |
| 50 | 0.11 | 0.15 | 0.27 | 0.80 | 1.18 | 1.18 | | | | | | | |
| 48 | 0.15 | 0.33 | 0.50 | 0.80 | 1.10 | 1.10 | | | | | | | |
| 18 | 0.10 | 0.32 | 0.53 | 0.94 | 1.16 | 1.16 | B | 0.25 | 0.41 | 0.54 | 0.80 | 1.05 | 1.08 |
| 17 | 0.08 | 0.11 | 0.28 | 0.84 | 1.08 | 1.15 | C | 0.18 | 0.22 | 0.28 | 0.72 | 1.05 | 1.15 |
| 51 | 0.10 | 0.11 | 0.20 | 0.84 | 1.18 | 1.18 | | | | | | | |
| 52 | 0.12 | 0.25 | 0.48 | 0.96 | 1.20 | 1.20 | | | | | | | |
| 19 | 0.08 | 0.09 | 0.15 | 0.80 | 1.10 | 1.16 | D | 0.22 | 0.33 | 0.50 | 0.78 | 1.05 | 1.14 |
| 4 | 0.18 | 0.40 | 0.68 | 0.90 | 1.18 | 1.20 | F | 0.11 | 0.15 | 0.23 | 0.80 | 1.15 | 1.20 |
| — | — | — | — | — | — | — | H | 0.07 | 0.06 | 0.06 | 0.14 | 0.99 | 1.23 |
| — | — | — | — | — | — | — | I | 0.15 | 0.17 | 0.26 | 0.76 | 1.19 | 1.24 |
| — | — | — | — | — | — | — | E | 0.10 | 0.10 | 0.12 | 0.44 | 1.10 | 1.18 |
| 14 | 0.09 | 0.15 | 0.34 | 0.89 | 1.10 | 1.14 | J | 0.16 | 0.20 | 0.30 | 0.74 | 1.16 | 1.18 |

From Table 4 it is clear that heat-sensitive recording sheets produced by using fluoran compounds of this invention, despite less coloration of texture, exhibit higher color-forming property than those produced by using fluoran compounds of prior art, contrary to the generally accepted theory that sheets with less coloration of texture suffer from poor color-forming property. This fact indicates that production of heat-sensitive recording sheets by use of fluoran compounds of this invention is highly advantageous.

Examples of Application

Example 1

In 100 parts of monoisopropyl biphenyl was dissolved 3 parts of 3-(N-methyl-N-n-amyl)-amino-6-methyl-7-anilinofluoran. The resultant solution was emulsified by addition of a solution of 20 parts of gum arabic in 160 parts of water. The emulsion was stirred with 20 parts of acid-treated gelatin and 160 parts of water added thereto, with the resultant mixture adjusted to pH 5 by addition of acetic acid. Subsequently, the mixture was subjected to coacervation in the presence of 500 parts of added water, with the result that a thick gelatin-gum arabic dope deposited in the form of coating film around the oil droplets of the color-forming compound dissolved in the solvent. The mixture was then adjusted to pH 4.4 and then mixed with 3.8 parts of an aqueous 37% formalin solution to solidify the liquid film mentioned above. It was then cooled to 10° C., adjusted to pH 9 by addition of an aqueous sodium hydroxide solution and left to stand at rest for five to six hours so as to enable the capsulation to proceed to perfection. The capsulated liquid thus obtained was applied to a sheet and dried. This sheet was brought into tight contact with a sheet coated with acid clay as an acidic electron-accepting adsorbent. When the paired sheets were exposed to the pressure applied by the tip of a ball-point pen or to the impact exerted by the types of a typewriter, an image of a blackish purple color appeared on the acid clay surface. The colored image showed high resistivity to light.

Example 2

The procedure of Example 1 was repeated, except that 3-(N-ethyl-N-β-ethylhexyl)amino-7-anilinofluoran dealt with in Synthesis 23 was used in place of 3-(N-methyl-N-n-amyl)-amino-6-methyl-7-anilinofluoran and alkyl naphthalene in place of monoisopropyl biphenyl respectively, to obtain a sheet coated with a mixture containing microcapsules. This sheet was brought into intimate contact with a sheet coated with phenol formalin resin as an acidic electron-accepting adsorbent. When the paired sheets were exposed to the pressure applied by the tip of a pen, there instantaneously appeared an image in a dense, dark green color. The colored image showed high resistivity to light.

Example 3

With 150 parts of an aqueous 10% polyvinyl alcohol solution and 65 parts of water, 30 parts of 3-(N-ethyl-N-iso-amyl)-amino-6-methyl-7-anilinofluoran touched upon in Synthesis 6 was mixed and disintegrated to form "Component A". After this disintegration, 3-(N-ethyl-N-iso-amyl)-amino-6-N-ethyl-7-anilinofluoran was found to have a particle diameter of 1 to 3 microns. Similarly, 35 parts of Bis-Phenol A, 150 parts of an aqueous 10% polyvinyl alcohol solution and 65 parts of water were mixed and disintegrated for one hour, to produce "Component B". After the disintegration, Bis-Phenol A was found to have a particle diameter of 1 to 3 microns.

Subsequently, 3 parts of Component A and 67 parts of Component B were mixed. The resultant mixture was spread on a sheet of paper and dried to produce a heat-sensitive recording sheet. The mixture in this case was applied at a rate of about 5 g/m². The heat-sensitive recording sheet thus obtained was free from spontaneous coloration and was substantially pure white. When it was exposed to heat applied by a heat pen, it instanteneously formed a black color. The colored image showed high resistivity to light and water.

Example 4

The procedure of Example 3 was repeated except that 3-(N-methyl-N-n-hexyl)-amino-6-methyl-7-anilinofluoran touched upon in Synthesis 10 was used instead, to afford "Component A". Separately, Bis-Phenol A was similarly treated to produce "Component B". Further, 35 parts of talc, 150 parts of an aqueous 10% polyvinyl alcohol solution and 65 parts of water were mixed and disintegrated to produce "Component C".

Subsequently, 3 parts of Component A, 27 parts of Component B and 40 parts of Component C were mixed and the resultant mixture was spread on a sheet of paper to obtain a heat-sensitive recording sheet. The heat-sensitive recording sheet was free from spontaneous coloration and was substantially pure white. When it was exposed to heat applied by a heat pen, it instantaneously formed a black color. When this sheet was overlaid by a thin sheet of paper containing an original drawn with a dye such as black ink which readily absorbs infrared rays and processed in an infrared-ray heat-sensitive copying machine, it abruptly produced an image in a black color, giving rise to a duplicate of the original.

Example 5

The procedure of Example 4 was repeated except that 3-(N-methyl-N-$\beta$-ethylhexyl)-amino-6-methyl-7-anilinofluoran touched upon in Synthesis 21 was used instead, to produce a substantially pure white heat-sensitive recording sheet free from spontaneous coloration. When this sheet was exposed to heat applied by means of a heat pen or a thermal head, it instantaneously formed a black color. The colored image showed high resistivity to light and humidity.

What is claimed is:

1. A chromogenic compound selected from the group consisting of 3-(N-ethyl-N-iso-amyl)-amino-6-methyl-7-anilinofluoran, 3-(N-methyl-N-n-hexyl)-amino-6-methyl-7-anilinofluoran and 3-(N-ethyl-N-n-hexyl)-amino-6-methyl-7-anilinofluoran.

2. A color developing composition suitable for use in heat-sensitive copying material, comprising at least one of the chromogenic compounds of claim 1 as color former, an electron-accepting substance, and a binder.

* * * * *

UNITED STATES PATENT AND TRADEMARK OFFICE
CERTIFICATE OF CORRECTION

PATENT NO. : 4,444,591

DATED : April 24, 1984

INVENTOR(S) : Hajime KAWAI, Katsuhiko TSUNEMITSU, Yoshiharu FUJINO, Yoji SHIMIZU It is certified that error appears in the above-identified patent and that said Letters Patent is hereby corrected as shown below:

| | Wrong | Correct |
|---|---|---|
| Title page, ABSTRACT and Column 1 (first and second formulas) | 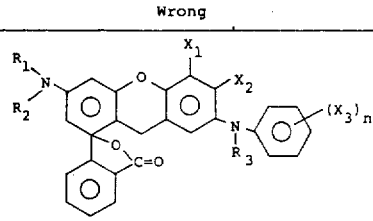 | 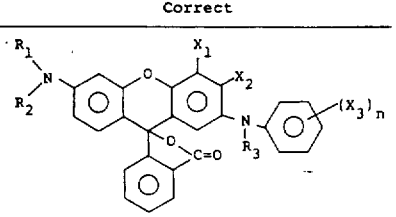 |
| Column 2 | 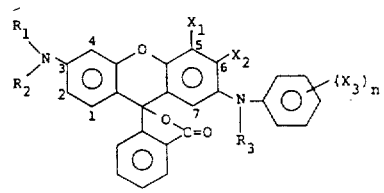 | 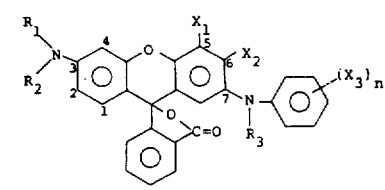 |
| Columns 25 and 26 (Product in Example No. 32) | 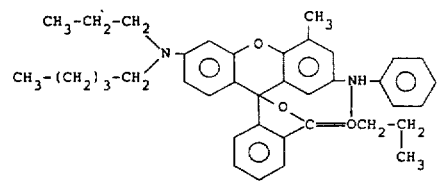 | 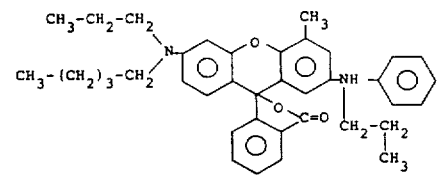 |

Signed and Sealed this

Fifth Day of January, 1993

*Attest:*

DOUGLAS B. COMER

*Attesting Officer*   *Acting Commissioner of Patents and Trademarks*